United States Patent [19]

Kamps-Holtzapple et al.

[11] Patent Number: 5,620,890
[45] Date of Patent: Apr. 15, 1997

[54] MONOCLONAL ANTIBODIES TO HYGROMYCIN B AND THE METHOD OF MAKING THE SAME

[75] Inventors: Carol Kamps-Holtzapple; Larry H. Stanker; John R. DeLoach, all of College Station, Tex.

[73] Assignee: The United States of America as represented by the Secretary of Agriculture, Washington, D.C.

[21] Appl. No.: 404,007

[22] Filed: Mar. 14, 1995

[51] Int. Cl.$^6$ .............................. C12N 5/12; C12N 15/06; C07K 16/44
[52] U.S. Cl. .................. 435/345; 530/388.9; 530/389.1; 530/389.8; 935/103; 935/104
[58] Field of Search ..................... 530/388.9, 389.1, 530/389.8; 435/240.27; 935/104, 103

[56] References Cited

PUBLICATIONS

Kamps–Holtzapple, C., et al., "Analysis of hapten–carrier protein conjugates by nondenaturing gel electrophoresis", *Journal of Immunological Methods*, 1993, 164, pp. 245–253.

Sheth, Hasmukh B. and Sporns, Peter, "Development of a single ELISA for Detection of Sulfonamides", *J. Agric. Food Chem.*, 1991, 39, pp. 1696–1700.

McAdam, David P., et al. "Mono– and Polyclonal Antibodies to the Organophosphate Fenitrothion. 1. Approaches to Hapten–Protein Conjugation", *J. Agric. Food Chem.*, 1992, 40, pp. 1466–1470.

Vallejo, Remo P., et al., "Effects of Hapten Structure and Bridging Groups on Antisera Specificity in Parathion Immunoassay Development", *J. Agric. Food Chem.*, 1982, 30, pp. 572–580.

Foglesong, Mark A. and LeFeber, Debra S., "Radioimmunoassay for Hygromycin B in Feeds", *J. Assoc. Off. Anal. Chem.*, 1982, vol. 65, No. 1, pp. 48–51.

Wie, Siong I. and Hammock, Bruce D., "Comparison of Coating and Immunizing Antigen Structure on the Sensitivity and Specificity of Immunoassays for Benzoylphenylurea Insecticides", *J. Agric. Food Chem.*, 1984, pp. 1294–1301.

Harrison, Robert O., et al., "Competitive Inhibition ELISA for the sTriazine Herbicides: Assay Optimization and Antibody Characterization", *J. Agric. Food Chem.*, 1991, 39, pp. 122–128.

Hastings, Kenneth L., et al., "Production and Characterization of a Monoclonal Antibody to Aflatoxin $B_2$", *J. Agric. Food Chem.*, 1988, 36, pp. 404–408.

Paxton, J.W., et al., "Production and Characterisation of Antisera to Diphenylhydantoin Suitable for Radioimmunoassay", *Journal of Immunological Methods*, 10, 1976, pp. 317–327.

J. Agric. Food Chem., 42:822, 1994, Holzapple et al.

Poultry Sci, 72(supp:1):63, 1993, Holzapple et al.

*Primary Examiner*—Frank C. Eisenschenk
*Attorney, Agent, or Firm*—M. Howard Silverstein; Curtis P. Ribando; John D. Fabo

[57] ABSTRACT

Hybridoma cell lines have been produced which secrete monoclonal antibodies that bind hygromycin B and are effective to detect hygromycin B levels as low as about 0.7 ppm. These monoclonal antibodies may be used for the detection and quantitative determination of trace amounts of hygromycin B in samples, especially in animal tissue and feed material.

11 Claims, 4 Drawing Sheets

MONOCLONAL ANTIBODIES TO HYGROMYCIN B AND THE METHOD OF MAKING THE SAME

BACKGROUND OF THE INVENTION

1. Field of the Invention

This invention relates to hybridoma cell lines and monoclonal antibodies produced therefrom which may be used to detect hygromycin B, particularly in animal tissues and feeds.

2. Description of the Prior Art

The anthelmintic, hygromycin B (HB), is an FDA approved feed additive used to control roundworms, nodular worms, and whipworms in swine, and large roundworms, cecal worms, and capillary worms in poultry. It is often used in conjunction with other drugs to increase the rate of weight gain and feed efficiency. Although approved as a feed additive, a zero tolerance level for hygromycin B in swine and poultry products (i.e. tissues, eggs) has been set by the FDA (21 CFR 556.330). For enforcement purposes, a residue limit of 1.4 ppm of the parent compound in the kidney has been established, and these limits are used by the U.S. Department of Agriculture/Food Safety Inspection Service (USDA/FSIS) to detect adulterated products. In order to comply with the regulations, medicated feed must be withdrawn 15 days prior to slaughter in swine and 3 days prior to slaughter in poultry.

Conventional methods for detection of hygromycin B in tissues include a microbiological assay (Johnston et al., *J. Food Prot.*, 1981, 44:828–831) and a high-performance liquid chromatography (HPLC) method (McLaughlin and Henion, *J. Chromatog.*, 1992, 59:195–206). The microbiological assay is nonspecific and requires long incubation periods. The HPLC method is labor intensive, has a multistep sample cleanup, and requires expensive equipment. A polyclonal-based radioimmunoassay (RIA) to detect hygromycin B in feed has been described (Foglesong and LeFeber, *J. Assoc. Off. Anal. Chem*, 1982, 65:48–51). This RIA overcomes some of the disadvantages of the previous methods, but it suffers from the problems associated with the need to continually synthesize unstable radiotracers and dispose of radiological waste. The disadvantages associated with these assay methods have prevented their being used for routine screening of large numbers of samples.

Enzyme-linked immunosorbent assays have been successfully developed as alternatives to the conventional microbiological or chemical methods for detection of pesticides (insecticides and herbicides), drug residues, and undesirable natural products (Azcona-Olivera et al., *J. Agric. Food Chem*, 1992, 40:531–534; Candlish et al., *J. Assoc. Off. Anal. Chem.*, 1988, 71:96–964; Degand et al., *J. Agric. Food Chem*, 1992, 40:70–75; Groopman et al., *Proc. Natl. Acad. Sci*, 1984, 81:7728–7731; Hu et al., *J. Food Prot.*, 1984, 47:126–127; Jung et al., *J. Agric. Food Chem.*, 1989, 37:1183–1187; Plhak and Sporns, *J. Agric. Food Chem.*, 1992, 40:2533–2540; Roseman et al., *J. Agric. Food Chem.*, 1992, 40:1008–1014; Shelby et al., *J. Agric. Food Chem.*, 1992, 40:1090–1092; Wong and Ahmed, *J. Agric. Food Chem.*, 1992: 40:811–816; Woychik et al., *Appl. Env. Microbiol.*, 1984, 48:1096–1099; Xu et al., *J. Assoc. Off. Anal. Chem.*, 1988, 71:945–948). In contrast to microbiological assays, immunoassays are highly specific (Stanker et al., *Toxicology*, 1987, 45:229–243; Vanderlaan et al., *Carcinogenesis*, 1988, 9:153–160; Van Emon et al., *Anal. Chem.*, 1985, 58:1866–1873), and unlike conventional chemical assays, they require minimal sample preparation procedures. However, an efficacious immunoassay requires high levels of specificity and sensitivity to the target agent.

In developing antibodies for use in feed contaminant immunoassays, various strategies have been employed in order to increase the probability that the antibodies will have high-affinity for the hapten. These strategies include (i) maintaining the structure of potentially important determinant groups on the hapten (Sheth and Sporns, *J. Agric. Food Chem.*, 1991, 39:1696–1700); (ii) using or extending the length of a linker arm (McAdam et al., *J. Agric. Food Chem.*, 1992, 40:1466–1470); and (iii) varying the immunization protocol (ie. mode of injection, number of injections, or length of immunization schedule) (Vallejo et al., *J. Agric. Food Chem.*, 1982, 30:572–580). Others also have reported effects of the linker arm length on the specificity and the sensitivity of the resulting antibodies (Wie and Hammock, *J. Agric. Food Chem.*, 1984, 32:1294–1301; Vallejo et al., (ibid.), Harrison et al., *J. Agric. Food Chem.*, 1991, 39:122–128; Sheth and Sporns, (ibid.). In general, for small haptens, extending the hapten away from the protein mass has been helpful or even critical to the production of high-affinity antibodies (Hastings et al., *J. Agric. Food Chem.*, 1988, 36:404–408; Paxton et al., *J. Immunol. Meth.*, 1976, 10:317–327). The factors that exactly control generation of a strong immune response, particularly to hygromycin B, are not clearly understood.

SUMMARY OF THE INVENTION

We have now discovered hybridoma cell lines which produce and secrete monoclonal antibodies which bind hygromycin B and are effective to detect hygromycin B at $IC_{50}$ values less than about 1.4 ppm. We have unexpectedly found that the high affinity monoclonal antibodies of this invention may be obtained by using a combination of a specifically modified immunization agent or immunogen and an extended immunization protocol. The monoclonal antibodies of this invention may be incorporated into kits for the detection and quantitative determination of low levels of hygromycin B in samples, especially in animal tissue and feed material. Detection of hygromycin B in sample materials is accomplished using immunosorbent assay procedures conventional in the art.

It is an object of this invention to provide hybridoma cell lines that produce and secrete high affinity monoclonal antibodies which selectively bind hygromycin B, and which are effective for detecting hygromycin B at very low levels.

It is also an object of the invention to provide a protocol for producing the aforementioned monoclonal antibodies in mice.

Another object of this invention is to provide immunoassay methods for the measurement of hygromycin B in animal tissue and feeds.

A further object is to provide kits useful for the assay of hygromycin B which include the monoclonal antibodies described herein.

Yet another object is to provide a method for recovering or removing hygromycin B from any material.

Other objects and advantages of this invention will become readily apparent from the ensuing description.

DEPOSIT OF BIOLOGICAL MATERIAL

Hybridoma cell line HB-13 was deposited on Aug. 13, 1996, under the terms of the Budapest Treaty at the American Type Culture Collection, 12301 Parklawn Drive, Rockville, Md. 20852, U.S.A., and has been assigned Accession No. ATCC HB-12167.

DETAILED DESCRIPTION OF THE INVENTION

In accordance with this invention we have created hybridoma cell lines that produce monoclonal antibodies which bind hygromycin B with high affinity and are effective for detecting and quantifying very low levels of the anthelmintic agent. By virtue of the novel protocol for raising them, the monoclonal antibodies of the invention possess significantly greater sensitivity than would otherwise be obtained, and they are capable of detecting hygromycin B levels less than about 1 ppm as determined by $IC_{50}$ in competitive inhibition ELISA.

Preparation of the hybridomas may be accomplished using conventional techniques such as described by Kohler and Milstein [Nature, 256:495–497 (1975)], Koprowski et al. [U.S. Pat. No. 4,196,265] or Wands [U.S. Pat. No. 4,271,145], the contents of each of which are incorporated by reference herein. Generally, the process of preparation comprises the steps of immunizing an animal with the antigen of interest, recovering splenocytes or lymphocytes from the animal, fusing the splenocytes or lymphocytes with continuously replicating myeloma cells to produce hybrid cells, and screening the resultant hybrid cells for the production of antibodies to the antigen. However, because hygromycin B is a relatively small molecule, it is itself incapable of stimulating the immune system to produce antibodies. To render the compound immunogenic, it must first be conjugated to an immunogenic carrier in such a manner that the resultant immunogen is capable of stimulating the immune system of an animal to produce specific antibodies that are capable of binding the unconjugated hygromycin B.

The structure of hygromycin B is as follows:

Hygromycin B

This compound is rendered immunogenic by coupling it to an immunogenic carrier using a heterobifunctional crosslinker by the following procedure.

Figure 1:
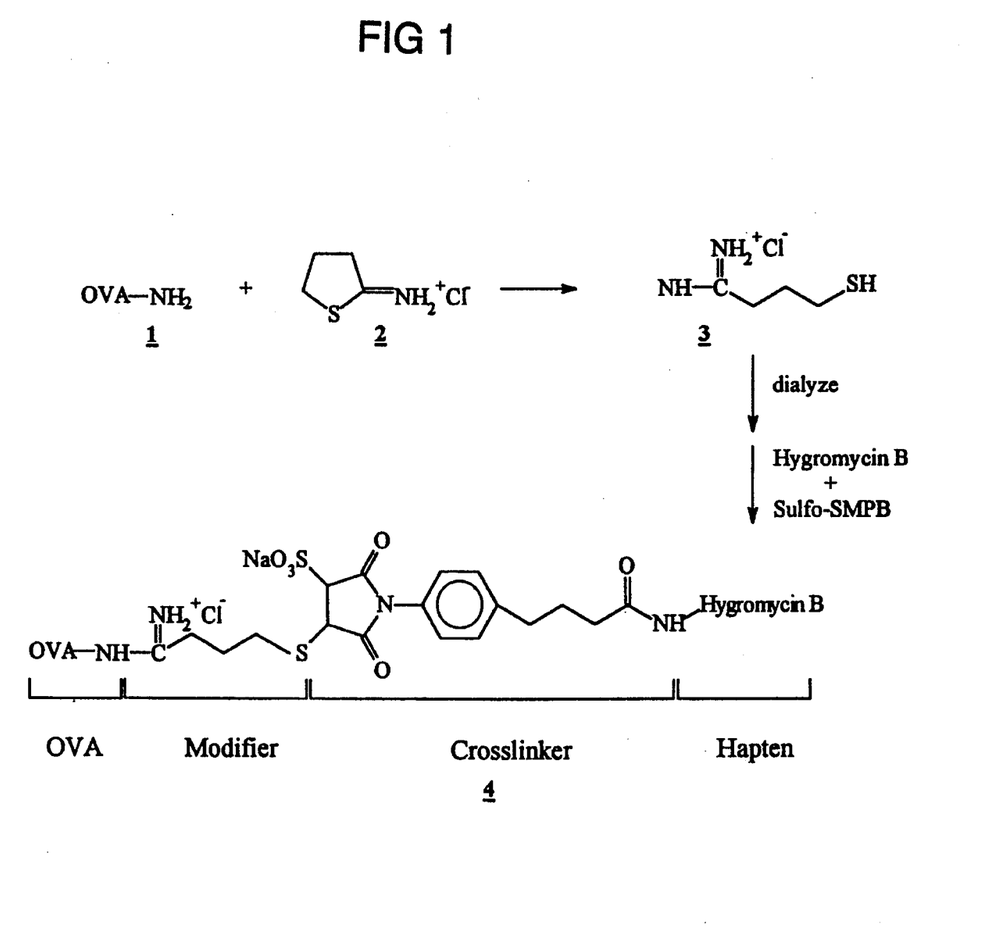
FIG. 1 shows the synthetic route to obtain hygromycin B-carrier protein conjugate using 2-iminothiolane to derivatize the carrier and sulfo-SMPB to link hygromycin B. The OVA conjugate produced using this scheme is designated HB-SMPB-S-OVA. (1) OVA; (2) 2-iminothiolane; (3) thiolated OVA; (4) HB-SMPB-S-OVA conjugate.

Immunogen. The immunizing agent is constructed as illustrated in FIG. 1 by covalently conjugating hygromycin B to an immunogenic carrier protein by means of a crosslinker. Immunogenic carriers are defined herein as any compound to which hygromycin B may be attached to render it immunogenic. Suitable carriers are well known and may be readily determined by the skilled practitioner in the art. Without being limited thereto, preferred carriers include proteins such as keyhole limpet hemocyanin (KLH), bovine serum albumin (BSA), ovalbumin (OVA) and human thyroglobulin. The function of the crosslinker is to introduce into the molecule a spacer of sufficient size to prevent the carrier protein from masking the hygromycin B molecule. That is, the hygromycin B must be sufficiently spaced from the carrier protein so that the component of the antigenic determinant contributed by the hygromycin B is available for recognition. It is envisioned that the spacer should comprise at least 10 atoms in its primary structure, with a preferred size of at least 16 atoms. These atoms would typically be selected from carbon, oxygen, nitrogen and sulfur and could be arranged in any of a variety of structures, including straight chain, ring, or combination thereof. The crosslinker described in the Examples below introduces a spacer having 16 atoms in its primary structure between the hygromycin B amino group and the amino group of the protein carrier.

As shown in FIG. 1, the method of conjugating the hygromycin B to the carrier involves a two step reaction. In the first step, the carrier protein is modified with 2-iminothiolane in order to introduce reactive free sulfhydryl groups into the protein. After removal of excess modifier by dialysis, hygromycin B and the heterobifunctional crosslinker, sulfo-succinimidyl-4-(p-maleidophenyl)butyrate (sulfo-SMPB), were added to the modified protein. In this step, it is advisable to use an excess of hygromycin B in relation to both the crosslinker and the modified protein in order to minimize the number of hygromycin B molecules that would be derivatized with two molecules of the crosslinker. The reactions are conducted in a suitable solvent such as phosphate buffered saline (PBS) under conditions which will promote the formation of the desired protein intermediate and conjugated hapten. The addition of ethylenediaminetetraacetic acid (EDTA) to the reaction medium in both steps prevents undesired disulfide bond formation. Alternative solvents include, but are not limited to, dimethylformamide (DMF), DMSO and dioxane. The reactions would normally be conducted under slightly alkaline conditions, but other conditions (e.g. temperature and time) are not critical and may be readily determined by the person of ordinary skill in the art.

Immunization. To generate antibody-producing splenocytes or lymphocytes, an immunizing preparation comprising the hygromycin B-carrier conjugate is injected into an immunologically competent animal. The preparation may also contain other proteins, although pure or substantially pure compositions of the conjugate in a pharmaceutically acceptable carrier are preferred.

Without being limited thereto, rats and particularly mice are preferred hosts for raising antibodies because of ease of handling. BALB/c mice are most commonly used. Preparation of hybridomas using splenocytes from these animals fused to any of a variety of myeloma cell lines, such as SP2/0, is well-known in the literature.

Certain aspects of the immunization protocol are critical to production of high affinity monoclonal antibodies. It is important that the injection schedule be sufficient to allow for maturation of the immune response in the animal. Preferably, a series of 3–4 injections should be given over a period of about 2 months prior to fusion. In the course of producing the HB-13 antibody described in detail in the Examples, below, injections were given on days 0, 14, 28 and about 58, with the last injection given 3–4 days prior to fusion. The dose of conjugate injected should of course be sufficient to stimulate the immune system. Extrapolating from the success of employing 75 µg conjugate per injection in the Examples below, it is anticipated that any reasonable amount in excess of about 25 µg per injection would also be effective. Typically, the conjugate is suspended in a physiological vehicle, such as isotonic saline or PBS buffer. In accordance with a preferred embodiment, an adjuvant may be incorporated into the immunizing preparation for enhanced stimulation of the immune system, particularly for the first 1–2 or 1–3 injections. A variety of adjuvants which are conventional in the art may be used herein, although Freund's or RIBI adjuvants are preferred. The route of injection is typically intraperitoneally, though other routes would also likely be effective in inducing an immune response.

Hybridization. Splenocytes or lymphocytes recovered from the immunized animal are fused with continuously replicating tumor cells, such as myeloma or lymphoma cells, cultured, and hybridoma cells selected using techniques conventional in the art. Many continuously replicating tumor cell lines are available which may be used as fusion partners with the splenocytes. Without being limited thereto, preferred myeloma cells include P3, NS1, K653, and particularly SP2/0.

Fusion and culture of the cells can be performed using conventional techniques. In accordance with one well known effective procedure, the splenocytes and myeloma cells are fused by exposure to polyethylene glycol. Hybrid cells are selected by culture in hypoxanthine-aminopterin-thymidine (HAT) medium, whereby unfused myeloma cells are killed by HAT and splenocytes die out, leaving only the hybrid cells. The resultant hybridomas are then grown in HAT or other suitable culture medium and assayed for antibody production.

Screening. Samples of the supernatant culture fluid from the hybridomas are screened for antibodies to hygromycin B. While the supernatants may be screened using a plurality of techniques such as RIA and ELISA, in accordance with the preferred embodiment of the invention, an indirect ELISA is employed. Generally, solid substrates, such as beads or the wells of a microtiter plate, which are coated with the antigen or antigen conjugate, are used to bind anti-hygromycin B antibody in the supernatants. Detection of bound antibody may be accomplished by addition of enzyme-labeled anti-immunoglobulin antibodies followed by enzyme substrate. Horse radish peroxidase and its substrate, 2,2'-azinobis-3-ethylbenthiazoline-sulfonic acid (ABTS) are preferred enzyme/substrate labels. However, it is understood that other enzyme/substrate labels or non-enzyme labels such as radiolabels or chromophores may also be used.

Cloning. Cloning of hybridomas which are positive for desired antibody production can be carried out as soon as they are detected by any method known in the art. Hybridomas having a positive response in the ELISA screen are preferably expanded and subcloned one or more times by limiting dilution to assure monoclonality.

The supernatant culture fluid from the cloned hybridomas may also be screened to select for those producing antibodies having a high affinity for hygromycin B. Affinity may be measured using a variety of well known techniques, such as ELISA, RIA or equilibrium dialysis using labelled hygromycin B. Competitive indirect ELISA (CI-ELISA) is preferred, and is conducted at a final antibody concentration (dilution from tissue culture supernatant) to give 50% of maximal binding to a hygromycin B coated substrate or assay well. In accordance with this embodiment, the antibody containing supernatant is added to a hygromycin B conjugate-coated solid substrate such as the wells of an assay plate, together with a range of concentrations of free hygromycin B as a competitor. Following incubation and washing, bound antibody in the wells is determined in the same manner as the indirect-ELISA. Percent inhibition may be calculated as $(1-B/B_o) \times 100$ where B is the optical density (OD) of a well with a competitor and $B_o$ is the mean OD of the wells without competitor (control). The relative affinity of the antibodies may be accurately measured as the concentration of free hygromycin B added to the wells that resulted in at least 20% inhibition ($IC_{20}$) of the control activity. However, for even greater accuracy, the affinity may be alternatively measured at 50% inhibition ($IC_{50}$).

Once hybridomas producing and secreting the desired anti-hygromycin B antibodies are identified, large quantities of the antibody may be produced in tissue culture using well-known techniques. Alternatively, antibody may be produced within host animals, such as by ascites formation in syngenic mice. Monoclonal antibodies so produced may be purified, for example, by affinity, chromatography on a protein A or G resin, or using hygromycin B bound to a resin.

The monoclonal antibodies produced in accordance with this invention possess very high affinity for hygromycin B, allowing the determination of the anthelmintic at very low levels, at least below the 1.4 ppm USDA/FSIS residue limit.

The monoclonal antibodies of this invention may be used to detect and quantify hygromycin B in unknown samples using well known immunosorbent assay procedures including but not limited to RIA or ELISA. A competitive inhibition ELISA similar to that used to screen the hybridomas is preferred. In this assay, a sample to be analyzed is incubated with the monoclonal antibody for hygromycin B and a solid substrate coated with hygromycin B conjugate. It is preferred to use a conjugate having a protein different from that used in the immunization protocol in order to avoid detection of antibodies to the protein carrier. After incubation, the solid phase is drained and washed, bound antibody on the coating antigen is detected, and percent inhibition is calculated as described earlier. The concentration of hygromycin B in the sample may then be determined by reference to a standard curve constructed from assays using known levels of hygromycin B.

In one alternative embodiment, hygromycin B may be determined by a competition ELISA such as described in Brandon et al. (U.S. Pat. No. 5,053,327, the contents of which are incorporated by reference herein) using the monoclonal antibody of the invention attached to a solid support.

For example, the anti-hygromycin B antibody may be immobilized on a bead or in a microtiter well. The unknown sample to be analyzed (or analytical standards of hygromycin B) are then added together with enzyme labeled or radiolabeled hygromycin B, and the amount of labeled hygromycin B bound to the antibody is then measured, using a substrate when the label is an enzyme. The amount of hygromycin B in the sample is inversely proportional to the amount of bound labeled hygromycin B. In another alternative, the monoclonal antibody may be attached to a solid support for use in conventional double-antibody sandwich ELISA procedures.

An assay using the antibodies of the invention would have the advantages of being more specific than a microbiological assay, and more rapid and less expensive than HPLC. It can be incorporated into a residue monitoring program as a rapid initial screen to eliminate samples that do not contain violative levels of hygromycin B. Therefore, use of this method to detect hygromycin B in kidney has the potential to increase sample throughput and to decrease costs associated with sample analyses.

With any of the above-described assay formats, the monoclonal antibodies of the invention may be incorporated into kits, alone or preferably together with any other necessary reagents. Such a kit for use herein comprises a first container comprising the monoclonal antibody, a second container comprising a detection reagent effective for detecting bound antibody, and hygromycin B conjugate bound to a solid support.

Determination of hygromycin B in animal tissue samples or feeds may be conducted using the above-described assay with minimal sample preparation and without extensive extraction procedures. Samples need only be homogenized in buffer, such as Tris-NaCl (pH 7.5) or digested in alkali and neutralized. The suspended sample is then centrifuged, and the liquid phase is recovered for use in the immunoassay. Although any animal tissue may be analyzed, the assay is particularly valuable for the determination of hygromycin B in meats and kidney. Tissue for analysis in accordance with the invention may originate from virtually any animal. Without being limited thereto, the analysis of tissue samples from domestic animals, including bovine, poultry and swine are encompassed by this invention.

Another application of the monoclonal antibodies is affinity purification of hygromycin B. The antibodies may be bound to a matrix, column, or other support using well-known techniques and used to recover or remove hygromycin B from any desired material. Alternatively, the antibodies may be incorporated into sensors such as solid phase electronic devices for detection of hygromycin B in sample materials.

The following examples are intended only to further illustrate the invention and are not intended to limit the scope of the invention which is defined by the claims.

EXAMPLE 1

Immunogen preparation (hapten synthesis)

Three conjugation methods were used to prepare hygromycin B-carrier protein conjugates, all of which couple an amine on the hapten to a reactive group on a carrier protein or a modified carrier. Conjugates were prepared with both OVA and BSA, the former used for the immunizations and the latter used as the coating antigen in the indirect ELISA described further, below. The hapten was coupled by: (1) direct carbodiimide-activated coupling to the carrier (no spacer); (2) oxime formation with a glutaraldehyde spacer arm on the glutarated-carrier (5 atom spacer); or (3) amide formation with the N-hydroxysuccinimide moiety of a heterobifunctional crosslinker and attachment of the hapten-crosslinker through the maleimide moiety of the crosslinker to sulfhydryl groups on the thiolated-carrier (16 atom spacer).

(1) Carbodiimide method. Hygromycin B (70 mg) was mixed with 10 mg carrier protein in 1.5 mL PBS, and to this mixture was added 14 mg 1-ethyl-3-(3-dimethylaminopropyl)-carbodiimide hydrochloride-carbodiimide (hereafter referred to as EDC or carbodiimide) as crosslinker. The excess of hygromycin B was used in order to minimize intra-protein crosslinking and maximize hapten attachment. The reaction mixture was stirred at room temperature overnight and then the sample was dialyzed against PBS.

(2) Glutarated-carrier method. In accordance with this approach, the carrier proteins are first reacted with glutaraldehyde in order to introduce 5-carbon reactive aldehyde groups into the proteins, and then the hygromycin B is attached to the other end of the 5-carbon spacers.

To 98 ml PBS was added 2.5 ml of 8% glutaraldehyde and 1 ml of a 10 mg/mL solution of carrier protein. The mixture was stirred overnight at 4° C. and then the volume was reduced to 15 mL by ultrafiltration using a 30,000 MW cut off stirred cell (Amicon; Beverly, MA). The ultrafiltration also separates the glutarated proteins from free glutaraldehyde, thereby minimizing the possibility that the glutaraldehyde would attach to the second amine on the hygromycin B. Hygromycin B (50 mg) was added to 5 mg of the glutarated-carrier protein, the reaction mixture was stirred overnight at 4° C., and the sample was then dialyzed against PBS.

(3) Thiolated-carrier method. In this method, carrier proteins were modified with 2-iminothiolane in order to introduce reactive free sulfhydryl groups into the protein. After removal of excess modifier by dialysis, hygromycin B and the heterobifunctional crosslinker, sulfo-succinimidyl-4-(p-maleidophenyl)-butyrate (sulfo-SMPB), were added to the modified protein (see conjugation scheme in FIG. 2).

Six milligrams of the protein modifier 2-iminothiolane-HCl (Traut's reagent) was added to 44 mg carrier protein in 2.2 mL PBS/0.1 M EDTA, pH 8.0. The EDTA was added to the buffer to prevent disulfide bond formation. After 24 h, 200 mL of 1M glycine was added to stop the addition of 2-iminothiolanee•HCl to the carrier protein. The samples were then dialyzed against PBS/0.1M EDTA, pH 8.0. A 5 mg sample of the thiolated-carrier in 0.5 mL PBS/0.1M EDTA, pH 8.0, was mixed with 35 mg of hygromycin B. The crosslinker, sulfo-SMPB (0.5 mg), was added and the solution was stirred overnight at room temperature. An excess of hygromycin B (compared to both the crosslinker and modified protein) was also used with this conjugation method in order to minimize the number of hygromycin B molecules that would be derivatized with two molecules of the crosslinker. The sample was then dialyzed against PBS. The BSA and OVA conjugates produced by this method were designated HB-SMPB-S-BSA and HB-SMPB-S-OVA, respectively.

Conjugation verification

Hygromycin B possesses no unique UV/vis absorbing group and cannot be easily removed from the carrier for quantitative analysis. Therefore, qualitative analysis of BSA conjugates prepared by the various methods described above was conducted using nondenaturing gel electrophoresis (Kamps-Holtzapple et al., 1993) to demonstrate that hygromycin B had been successfully conjugated (results not shown). In each case, the migration of the HB-BSA conjugate was distinct from both that of the free carrier protein and also from that of the carrier protein treated with crosslinker alone (methods 1 and 3) or from the carrier protein alone (method 2 wherein no crosslinker is needed).

EXAMPLE 2

Hybridoma and Monoclonal Antibody Production

In the short immunization schedule, female BALB/c mice (6–8 weeks of age) were injected intraperitoneally (ip) with 75 µg of HB-SMPB-S-OVA (in 0.2 mL physiological saline/ RIBI adjuvant). The mice received a second ip injection after three weeks. One week after the second injection, the mice were bled and serum titers were determined. Five weeks after the initial immunization (three days before the fusion), a third 75 µg ip injection of the immunogen in PBS (without adjuvant) was administered.

In the extended immunization schedule, female BALB/c mice were immunized with 75 µg ip injections every two weeks for a total of three injections. On day 35, the mice were bled so that serum titers and antibody specificities could be determined. No injections were administered for one month, and then a final 75 µg ip dose of the immunogen in PBS (no adjuvant) was administered 4 days prior to the fusion.

Splenocytes from an immunized mouse were fused with SP2/0 myeloma cells using PEG (Stanker et al., 1986). Fused cells were resuspended in HAT medium (Iscove's modified Dulbecco's medium containing 36 mM $NaHCO_3$, 2 mM glutamine, 100 units/mL penicillin, 100 µg/mL streptomycin, 5% fetal bovine serum, 100 mM hypoxanthine, 0.2 mM aminopterin, and 8 mM thymidine) and pipetted into the wells of twenty-three 96-well plates containing a feeder layer of mouse macrophages. Growing hybridomas were observed in greater than 90% of the wells 10 days after fusion. After 10–14 days, hybridoma supernatants were analyzed by indirect ELISA for the presence of antibodies against hygromycin B.

Indirect ELISA for hybridoma selection

Wells of polystyrene microtiter plates were coated with 100 µL of the coating antigen, HB-SMPB-S-BSA (1 µg/mL), and air-dried overnight at 40° C. The BSA conjugate was used as the solid-phase antigen in order to avoid detection of antibodies to the OVA carrier used to immunize the animals. Nonspecific binding was decreased by blocking the wells with 3% (w/v) non-fat milk solution in deionized water for 30 min at 37° C. After five washes with 0.05% Tween 20 in distilled water, 100 µL of the appropriate serum or cell culture supernatant dilutions were allowed to bind to the coated microwells for 90 min at 37° C. Unbound antibody was removed by washing five times with the 0.05% Tween 20-water solution. Next, 50 µL of goat anti-mouse IgG-peroxidase conjugate (1:500 dilution) was added to each well. After a 60 min incubation at 37° C., the plates were washed ten times with 0.05% Tween 20, and bound antibody-peroxidase conjugate was determined using the colorimetric substrate, ABTS. Absorbance was read at 405 nm.

Hybridoma expansion

Cells in fusion wells with supernatants exhibiting inhibition (80 wells) were transferred from the fusion plates to 24-well plates. Cultures showing the highest percentage of inhibition were cloned twice by limiting dilution (Goding, 1983). For each cloning procedure, the cells were plated in HT medium on a layer of macrophage feeder cells, and final clones were obtained from wells that had been seeded with one (or fewer) cell per well.

Competitive indirect ELISA for evaluating sensitivity and specificity

A competitive indirect ELISA (CI-ELISA) was used to determine the sensitivity and specificity of the monoclonal antibodies for binding hygromycin B. Microtiter plates were coated with HB-SMPB-S-BSA (400 ng/well) and blocked with 3% non-fat milk solution as described above. After washing five times with 0.05% Tween 20 in distilled water, 100 µL of hygromycin B standard in assay buffer (0.1M Tris, 0.15M NaCl, 0.05% Tween 20, 1% BSA, pH 7.5) and 100 µL antiserum (diluted 1:60 in assay buffer) were added to each well and incubated for 90 min at 37° C. Unbound antibody was removed by washing five times with the 0.05% Tween 20-water solution. Next, 50 µL of goat anti-mouse IgG-peroxidase conjugate (1:500 dilution) was added to each well. After a 60 min incubation at 37° C., the plates were washed ten times with 0.05% Tween 20, and bound antibody-peroxidase conjugate was determined using ABTS. Absorbance was read at 405 nm.

Only 7 of the original 80 picks resulted in stable hybridomas secreting antibodies against free hygromycin B. Cells from these seven were subcloned and monoclonal cell lines secreting anti-hygromycin B antibodies were established. All of the monoclonal antibodies were determined to be IgG1 antibodies with K light chains.

Discussion of Example 2

Figure 2:
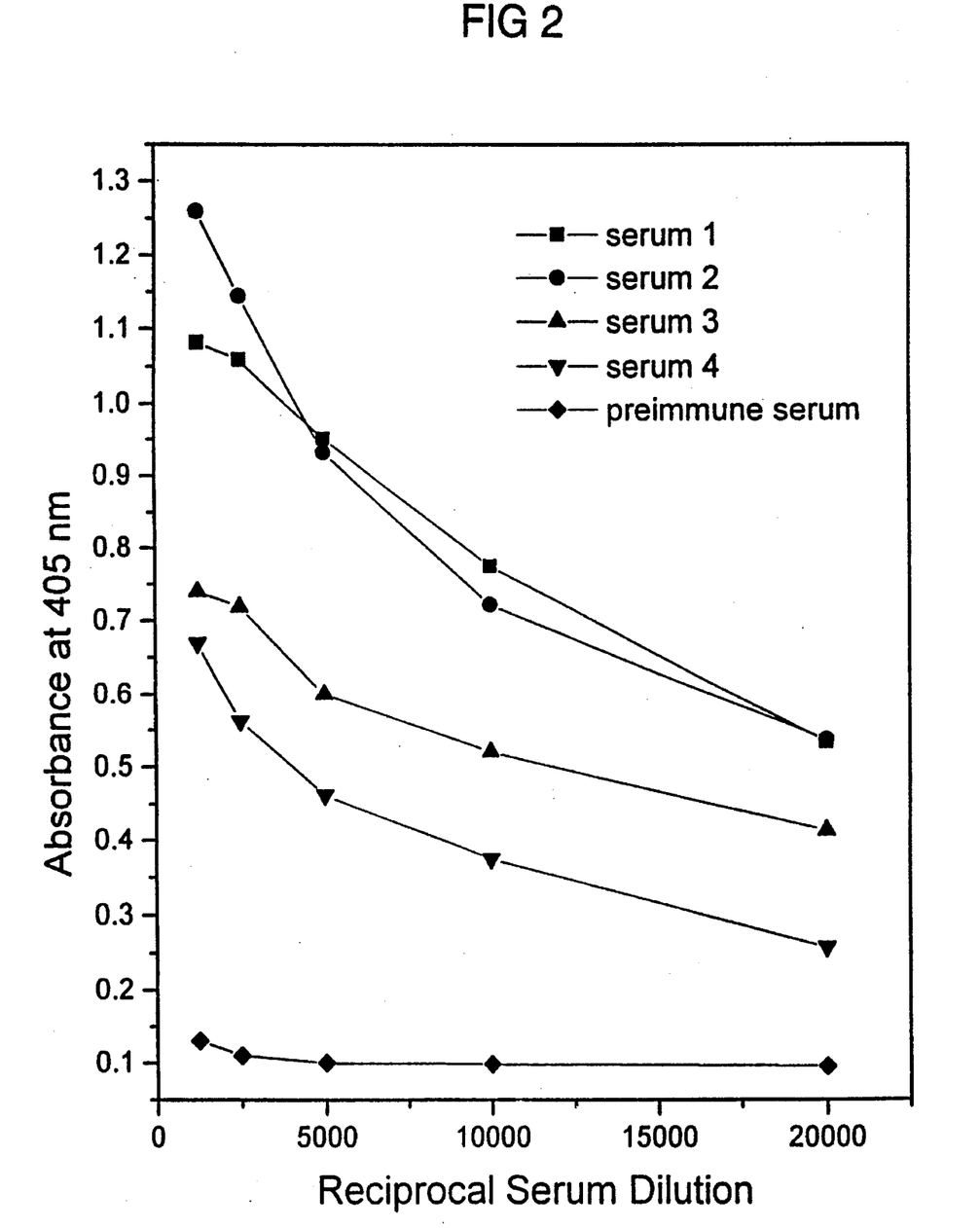
FIG. 2 shows titration curves of sera from mice immunized with HB-SMPB-S-OVA. Titers were determined by indirect ELISA using HB-SMPB-S-BSA as the solid phase coating antigen.

Although qualitative analysis of the conjugates demonstrated that hygromycin B had been successfully conjugated to the carrier proteins, none of the mice treated with hygromycin B conjugated directly to the carrier protein using carbodiimide (no linkage arm) or with hygromycin B conjugated to glutaraldehyde-treated carrier protein (5-atom linkage arm) produced antibodies to free hygromycin B (data not shown). In contrast, mice immunized with hygromycin B conjugated to 2-iminothiolane-modified carrier using the crosslinker, sulfo-SMPB, resulted in antibody serum titers greater than 20,000. FIG. 2 presents the results of the analysis of the serum from four mice injected with the HB-SMPB-S-OVA conjugate. In these experiments, the titer was defined as the reciprocal of the dilution that results in an absorbance value that is twice that of background. It is possible that hygromycin B, when linked directly to the carrier, was masked to a large extent by the surrounding protein. It is unclear why the hygromycin B conjugated with a 5-atom linker failed to generate an immune response. Since hygromycin B contains two reactive amines, many of the hapten molecules may have been conjugated by two reactive aldehyde groups on the glutarated carrier protein. It is clear, however, that the sulfo-SMPB-linked hapten possessed the necessary design for raising antibodies to hygromycin B.

In attempting to produce antibodies to hygromycin B, we found that when the immunization protocol originally recommended by the adjuvant manufacturer was used (injections on days 0 and 21, serum titer determination on day 26, and a final injection on day 35, 3–4 days before fusion), the monoclonal antibodies that were produced exhibited low affinity for hygromycin B ($IC_{50}$ ranging from 10–100 ppm). This same protocol has been used to successfully produce high affinity antibodies ($IC_{50}$ ranging from 0.1–20 ppb) to other haptens being investigated in our laboratory (unpublished data). However, higher affinity antibodies to hygromycin B were obtained after an extended immunization protocol was used (injections on day 0, 14, 28, serum titer determination day 35, one month of no injections and an injection 3–4 days before fusion). Adding an additional injection (containing adjuvant) and incorporating a one-month rest period into the immunization protocol resulted in production of antibodies with a 12-fold increase in sensitivity to hygromycin B (ie. $IC_{50}$ values of 0.7–1 ppm).

Figure 3:
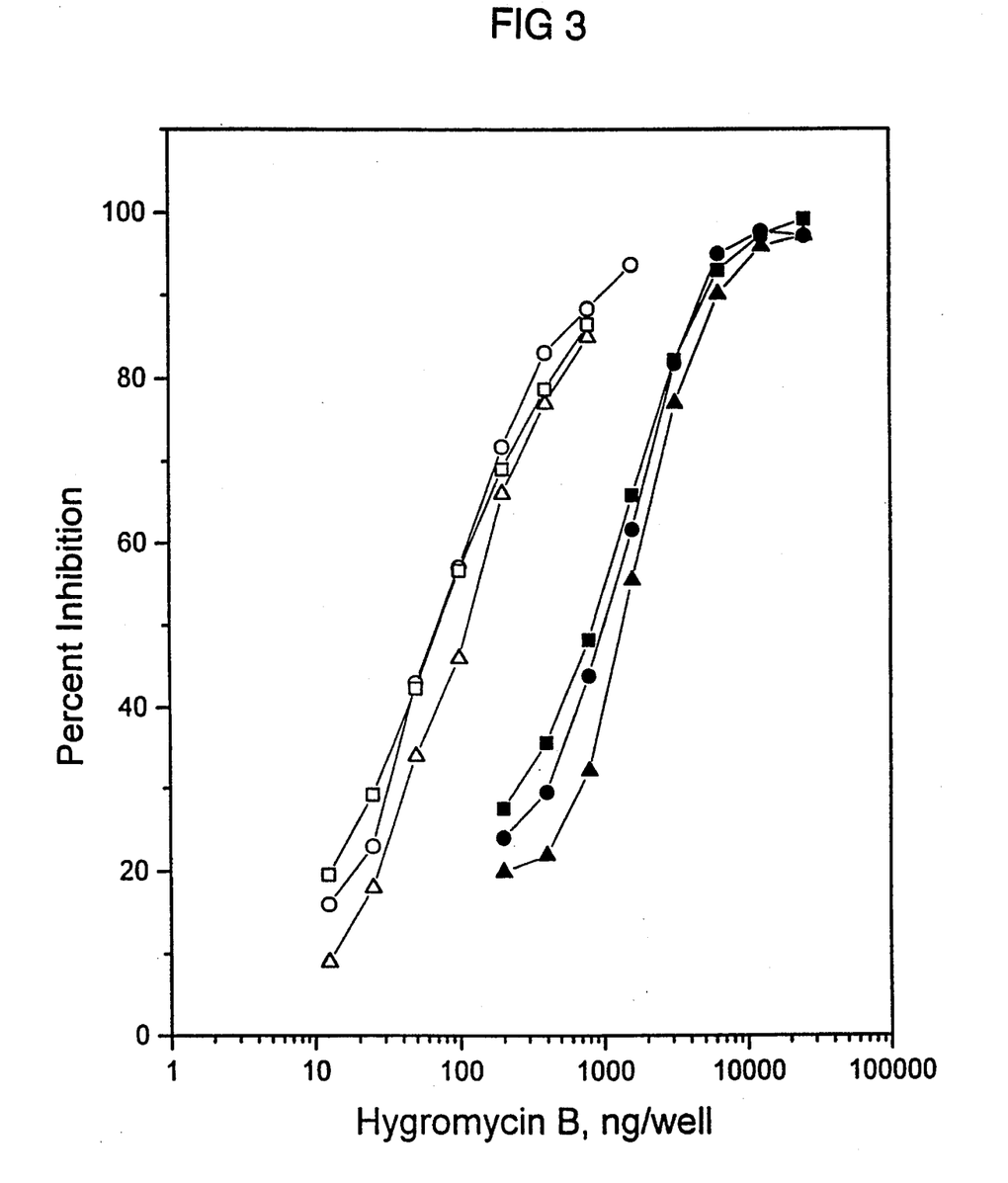
FIG. 3 shows representative inhibition curves of the 3 most sensitive monoclonal antibodies obtained using the short immunization protocol (closed symbols) or the extended immunization protocol (open symbols). Inhibition curves were generated using a competitive indirect ELISA.

Representative competition ELISA curves for the three most sensitive antibodies obtained using the two immunization schedules are shown in FIG. 3. The antibodies obtained using the short immunization protocol are represented by closed symbols and those obtained by the extended immunization protocol are represented by open symbols. Three of these antibodies, designated HB-3, HB-7 and HB-13, are represented by the open triangles, circles and squares, respectively.

The HB-13 Antibody

Antibody HB-13 was the most sensitive antibody obtained using the extended immunization protocol and was chosen for development of an ELISA to detect hygromycin B. The hybridoma cell line HB-13 producing this antibody has been deposited in the ATTC depository and has been assigned Accession No. HB-12167.

Figure 4:
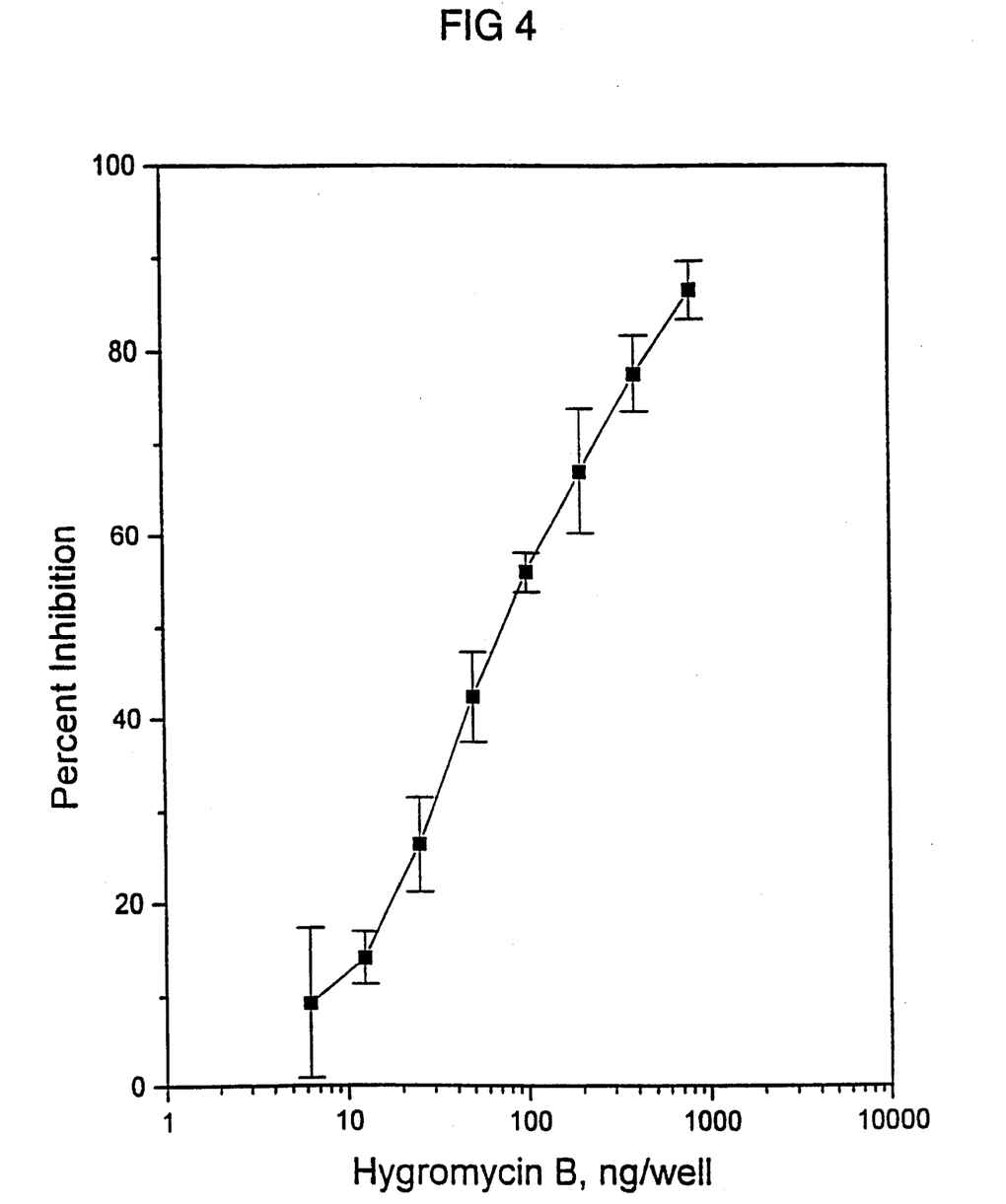
FIG. 4 shows competitive indirect ELISA standard curve for hygromycin B using monoclonal antibody HB-13. The solid-phase antigen was HB-SMPB-S-BSA. Error bars represent ±1 standard deviation.

A representative inhibition curve for HB-13 obtained in the CI-ELISA, using hygromycin B as competitor, is shown in FIG. 4. Each point represents the average of 6 replicates. The average $IC_{50}$ observed for hygromycin B was 76.2 ng/well (0.762 ppm). The mean intraassay $IC_{50}$ coefficient of variation (CV) was 7.8% (n=3), while a mean interassay $IC_{50}$ coefficient of variation of 7.0% (n=3) was observed. The detection limit of the assay (defined as the lowest concentration of hygromycin B exhibiting O.D. readings that were lower than that of the zero standard by twice the standard deviation of the zero standard) was 25 ng/well or 250 ng/mL (0.25 ppm). HB-13 was also characterized as to its ability to recognize related aminoglycoside antibiotics, including spiramycin, gentamicin, kanamycin, amikacin and tylosin. None of these compounds were observed to cross-react with the HB-13 antibody in the competitive indirect ELISA (using a competitor concentration of 50 ppm).

EXAMPLE 3

Kidney extract preparation

CI-ELISA was used to detect hygromycinB in porcine kidney extracts. Minced samples (5 g) of hygromycin-free kidney (obtained from the Texas A & M University Swine Center) were spiked with hygromycin B at concentrations of 1, 2 or 4 ppm (μg/g) and were kept frozen until analysis. In order to prepare spiked samples for analysis, the samples were digested with 5 mL 2N NaOH for 45 min at 37° C., diluted with 8.2 mL deionized water and neutralized to a final pH of 6.5–7.0 with 1.8 mL 6N HCl. Following centrifugation at 14,000×g for 45 min at 4° C., the supernatants were added directly to the microtiter plates and analyzed by CI-ELISA. As shown in Table I, below, the samples spiked at 1, 2, and 4 ppm (μg/g) gave mean recoveries of 83, 82 and 91% respectively.

It is understood that the foregoing detailed description is given merely by way of illustration and that modifications and variations may be made therein without departing from the spirit and scope of the invention.

TABLE I

Recovery of Hygromycin B from Spiked Kidney by Competitive Indirect ELISA

| hygromycin B added, ppm (μg/g) | sample[1] | recovery ppm (μg/g)[2] | %[3] |
|---|---|---|---|
| 0 | A | nd[4] | — |
| 0 | B | nd | — |
| 0 | C | nd | — |
| 1 | A | 1.1 ± 0.4 | 110 |
| 1 | B | 0.6 ± 0.1 | 60 |
| 1 | C | 0.8 ± 0.2 | 80 |
| 2 | A | 1.6 ± 0.5 | 80 |
| 2 | B | 1.5 ± 0.4 | 75 |
| 2 | C | 1.8 ± 1.0 | 90 |
| 4 | A | 3.3 ± 0.6 | 83 |
| 4 | B | 3.5 ± 1.1 | 88 |
| 4 | C | 4.1 ± 1.8 | 103 |

[1] Samples were spiked separately in triplicate and assayed on separate days (A–C).
[2] Mean recoveries (n = 3) for samples containing 1, 2, or 4 ppm (μg/g) hygromycin B were 0.8, 1.6, and 3.6 ppm, respectively.
[3] Mean percent recoveries (n = 3) for 1, 2, and 4 ppm were 83, 82, and 91%, respectively.
[4] None detected (less than 0.25 ppm, the detection limit of this assay).

We claim:

1. A hybridoma cell line which produces and secretes monoclonal antibodies which bind hygromycin B and are effective to detect hygromycin B levels at about 1.4 ppm or lower.

2. A hybridoma cell line which produces and secretes monoclonal antibodies which bind hygromycin B and are effective to detect hygromycin B levels at about 1.4 ppm or lower, wherein the hybridoma cell line is produced using an immunization preparation comprising hygromycin B conjugated to an immunogenic carrier through a spacer of more than 5 atoms, wherein th spacer prevents the masking of hygromycin B by the carrier protein, and and immunization protocol comprising at least three injection over a period of two months.

3. The hybridoma cell line of claim 2 wherein said spacer is 16 atoms.

4. The hybridoma cell line of claim 3 wherein said preparation is formed by the process comprising reacting hygromycin B with sulfo-succinimidyl-4-(p-maleidophenyl)-butyrate (sulfo-SMPB) in the presence of a protein carrier derivatized with 2-iminothiolane•HCl under conditions effective to form hygromycin B-SMPB-S-carrier protein conjugate.

5. The hybridoma cell line of claim 1, wherein said cell line is HB-13.

6. A monoclonal antibody produced by the hybridoma cell line of claim 1.

7. A monoclonal antibody produced by the hybridoma cell line of claim 4.

8. A monoclonal antibody produced by the hybridoma cell line of claim 5.

9. A kit for detecting hygromycin B in animal tissue or feed material comrising the monoclonal antibody of claim 6 and a reagent for detecting said antibody.

10. A kit for detecting hygromycin B in animal tissue or feed material comprising the monoclonal antibody of claim 8 and a reagent for detecting said antibody.

11. A kit for detecting hygromycin B in animal tissue or feed material comprising the monoclonal antibody of claim 7 and a reagent for detecting said antibody.

* * * * *